United States Patent
Case et al.

(10) Patent No.: US 10,555,095 B2
(45) Date of Patent: Feb. 4, 2020

(54) HEARING AID ADAPTER

(71) Applicant: Cochlear Limited, Macquarie University, NSW (AU)

(72) Inventors: Alexander Case, Enmore (AU); Michael Goorevich, Naremburn (AU)

(73) Assignee: Cochlear Limited, Macquarie University, NSW (AU)

( * ) Notice: Subject to any disclaimer, the term of this patent is extended or adjusted under 35 U.S.C. 154(b) by 37 days.

(21) Appl. No.: 15/245,543

(22) Filed: Aug. 24, 2016

(65) Prior Publication Data
US 2018/0063655 A1 Mar. 1, 2018

(51) Int. Cl.
*H04R 25/00* (2006.01)
*A61F 2/18* (2006.01)
*A61N 1/05* (2006.01)

(52) U.S. Cl.
CPC ............ *H04R 25/554* (2013.01); *A61F 2/18* (2013.01); *A61N 1/0541* (2013.01); *H04R 25/505* (2013.01); *H04R 25/556* (2013.01); *H04R 25/606* (2013.01); *H04R 2225/021* (2013.01); *H04R 2225/67* (2013.01)

(58) Field of Classification Search
CPC .. H04R 25/554; H04R 25/558; H04R 25/604; H04R 25/606; H04R 2225/021; H04R 2225/025; H04R 2225/51; H04R 2225/63; H04R 2225/67; H04R 2460/13; A61N 1/36036; A61N 1/37229
USPC ....... 381/312, 314, 315, 316, 322, 323, 324, 381/326, 328, 330, 331, 381; 600/25; 607/55, 56, 57
See application file for complete search history.

(56) References Cited

U.S. PATENT DOCUMENTS

| 3,764,748 A * | 10/1973 | Branch ............... H04R 25/606 381/190 |
| 5,824,022 A * | 10/1998 | Zilberman ......... A61N 1/36036 128/903 |
| 7,599,508 B1 * | 10/2009 | Lynch ................. H04R 25/00 381/312 |
| 8,706,246 B2 | 4/2014 | Mishra |
| 8,706,247 B2 | 4/2014 | Mishra et al. |
| 8,923,541 B2 | 12/2014 | Mishra et al. |
| 8,942,815 B2 | 1/2015 | Chung et al. |
| 2005/0033384 A1 * | 2/2005 | Sacha ................ A61N 1/36036 607/57 |
| 2005/0209657 A1 | 9/2005 | Chung et al. |

(Continued)

FOREIGN PATENT DOCUMENTS

KR 20090076484 A 7/2009

OTHER PUBLICATIONS

International Search Report and Written Opinion in corresponding International Application No. PCT/IB2017/054949, dated Dec. 14, 2017, 10 pages.

*Primary Examiner* — Huyen D Le
(74) *Attorney, Agent, or Firm* — Edell, Shapiro & Finnan, LLC

(57) ABSTRACT

Presented herein are stand-alone hearing aid adapters configured to enable the use of the recipient's hearing aid to detect and process ambient sound signals and to convert output signals generated by the acoustic hearing aid into input signals useable by the implantable hearing prosthesis for generation and delivery of stimulation to a recipient.

20 Claims, 7 Drawing Sheets

(56) References Cited

U.S. PATENT DOCUMENTS

2012/0041515 A1* 2/2012 Meskens ............ A61N 1/37229
607/57
2013/0274826 A1   10/2013 Darley et al.
2015/0367132 A1   12/2015 Milczynski et al.

* cited by examiner

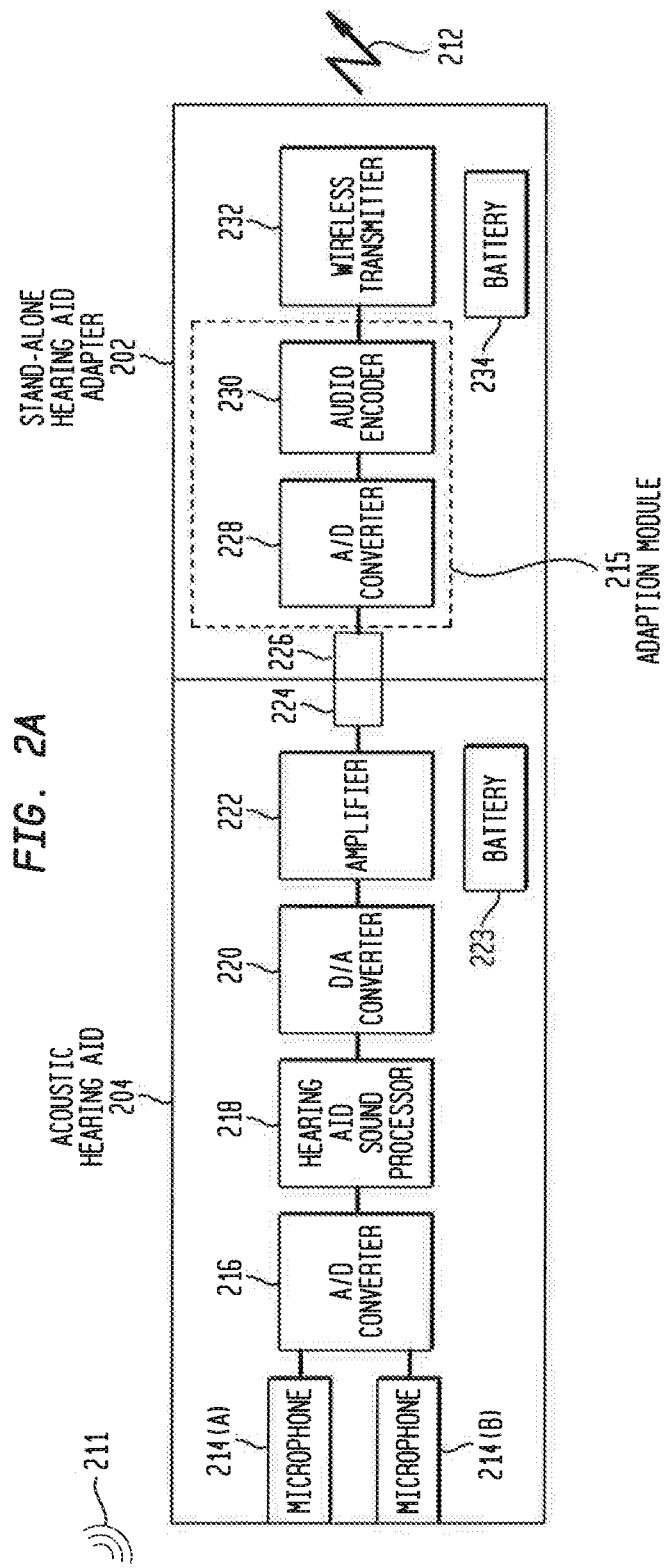

HEARING AID ADAPTER

BACKGROUND

Field of the Invention

The present invention relates generally to hearing prostheses.

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. An auditory brainstem stimulator is another type of stimulating auditory prosthesis that might also be proposed when a recipient experiences sensorineural hearing loss due to damage to the auditory nerve.

SUMMARY

In one aspect, a stand-alone hearing aid adapter is provided. The stand-alone hearing aid adapter comprises: at least one input element configured to receive hearing aid output signals from an acoustic hearing aid; an adaption module configured to convert the hearing aid output signals into implantable hearing prosthesis input signals; and a wireless transmitter configured to transmit the implantable hearing prosthesis input signals to an implantable hearing prosthesis.

In another aspect, a method is provided. The method comprises: receiving, at a hearing aid adapter in communication with an acoustic hearing aid, hearing aid output signals generated by the acoustic hearing aid based on detected sound signals; converting, with the hearing aid adapter, the hearing aid output signals into implantable hearing prosthesis input signals; and wirelessly transmitting the implantable hearing prosthesis input signals from the hearing aid adapter to an implantable hearing prosthesis.

In another aspect, an implantable hearing prosthesis system is provided. The implantable hearing prosthesis system comprises: an implantable hearing prosthesis configured to be at least partially implanted in a recipient; and a stand-alone hearing aid adapter configured to be coupled with an acoustic hearing aid and to wirelessly stream processed sound signals from the acoustic hearing aid to the implantable hearing prosthesis.

BRIEF DESCRIPTION OF THE DRAWINGS

Embodiments of the present invention are described herein in conjunction with the accompanying drawings, in which:

FIG. 2A is a block diagram of a stand-alone hearing aid adapter in accordance with embodiments presented herein;

DETAILED DESCRIPTION

Figure 1:
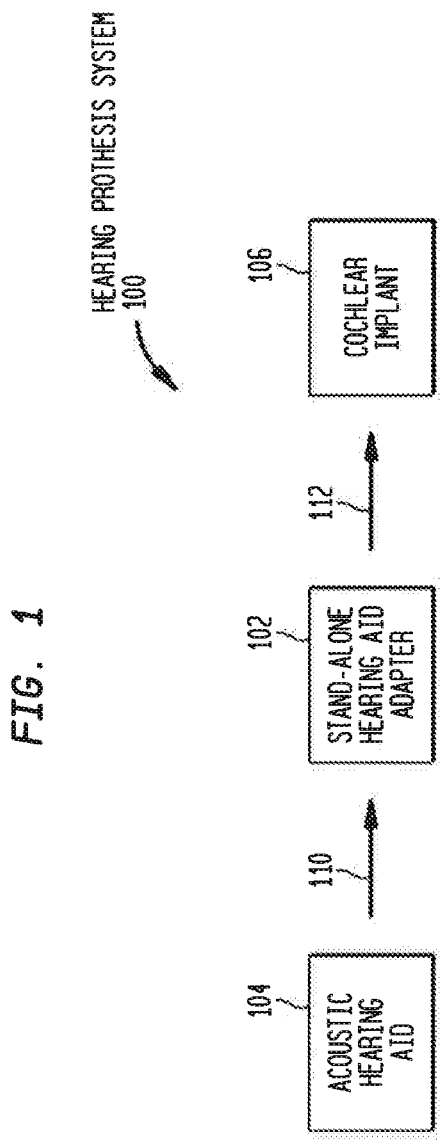
FIG. 1 is a block diagram illustrating a hearing prosthesis system that includes a stand-alone hearing aid adapter in accordance with embodiments presented herein.

Individuals may suffer from different types and/or degrees of hearing loss, including conductive and/or sensorineural hearing loss. These different types and/or degrees of hearing loss may be treated in different manners. For example, conductive hearing loss is commonly treated with acoustic hearing aids that are designed to deliver amplified acoustic signals to a recipient's inner ear. In contrast, sensorineural hearing loss is generally treated using implantable hearing/auditory prostheses, such as cochlear implants, auditory brainstem, etc., that directly stimulate nerve cells of the recipient's auditory system.

In certain cases, an individual may experience changes in his/her hearing loss that results in the need to transition from a hearing aid treatment regime (i.e., the use of an acoustic hearing aid) to an implantable treatment regime (i.e., use of an implantable hearing prosthesis). That is, certain recipients of acoustic hearing aids may, over time, be unable to continue to derive suitable benefit from their acoustic hearing aid(s). In conventional techniques, these individuals are required to discard their familiar (and often expensive) acoustic hearing aid, along with its accompanying user interface, accessories, remote controls, etc. and immediately adjust to use of a complete implantable hearing prosthesis. However, implantable hearing prostheses commonly include user interfaces that are different from those of the recipient's hearing aid, as well as often utilize different accessories, remote controls, etc. The requirement for a recipient to immediately make these adjustments not only makes the recipient's transition from the acoustic hearing aid to the implantable hearing prosthesis difficult, but can also act as a financial or other impediment to initiating the transition.

Hearing aid form factors and processors offer a wide set of processing options. Unfortunately, it is difficult to re-use hearing aid technology within an implantable system due to the prevalence of different operating platforms between hearing aids and implantable systems which are often produced by different manufacturers. Accordingly, there currently exists no practical way to combine an acoustic hearing aid with an implantable hearing prosthesis (such as a cochlear implant) for use by a recipient to perceive sounds.

Presented herein are techniques and associated devices, referred to herein as stand-alone hearing aid adapters or simply hearing aid adapters, that are designed to enable a recipient to continue to use his/her existing acoustic hearing aid even after receiving an implantable hearing prosthesis (e.g., when transitioning from a hearing aid solution to an implantable solution). In particular, the stand-alone hearing aid adapters presented herein are configured to enable the use of the recipient's hearing aid to detect and process ambient sound signals. The stand-alone hearing aid adapters are also configured to convert output signals generated by the acoustic hearing aid into input signals useable by the implantable hearing prosthesis for generation and delivery of stimulation to the recipient's nerve cells. As a result, the implantable hearing prosthesis receives signals that have been detected by the sound input elements (e.g., microphones) of the acoustic hearing aid, and signals which have already undergone sound processing within the hearing aid.

For ease of illustration, embodiments are primarily described herein with reference to stand-alone hearing aid adapters for connecting an acoustic hearing aid with one specific type of implantable hearing prosthesis, namely a cochlear implant. However, it is to be appreciated that the stand-alone hearing aid adapters presented herein may be used to connect hearing aids with other types of hearing prostheses, such as auditory brainstem stimulators.

FIG. 1 is block diagram of an exemplary hearing prosthesis system 100 that includes a stand-alone hearing aid adapter 102 configured to retrofit an acoustic hearing aid 104 to provide input signals to a cochlear implant 106. In particular, and as described further below, the stand-alone hearing aid adapter 102 is configured to replace an acoustic receiver of the acoustic hearing aid 104 such that hearing aid output signals 110 are resampled and converted into cochlear implant input signals 112. The stand-alone hearing aid adapter 102 is further configured to provide the cochlear implant input signals 112 to the cochlear implant 106. As described further below, the cochlear implant input signals 112 may, in certain embodiments, be wirelessly transmitted to an external or implanted component of the cochlear implant 106.

Figure 2B:
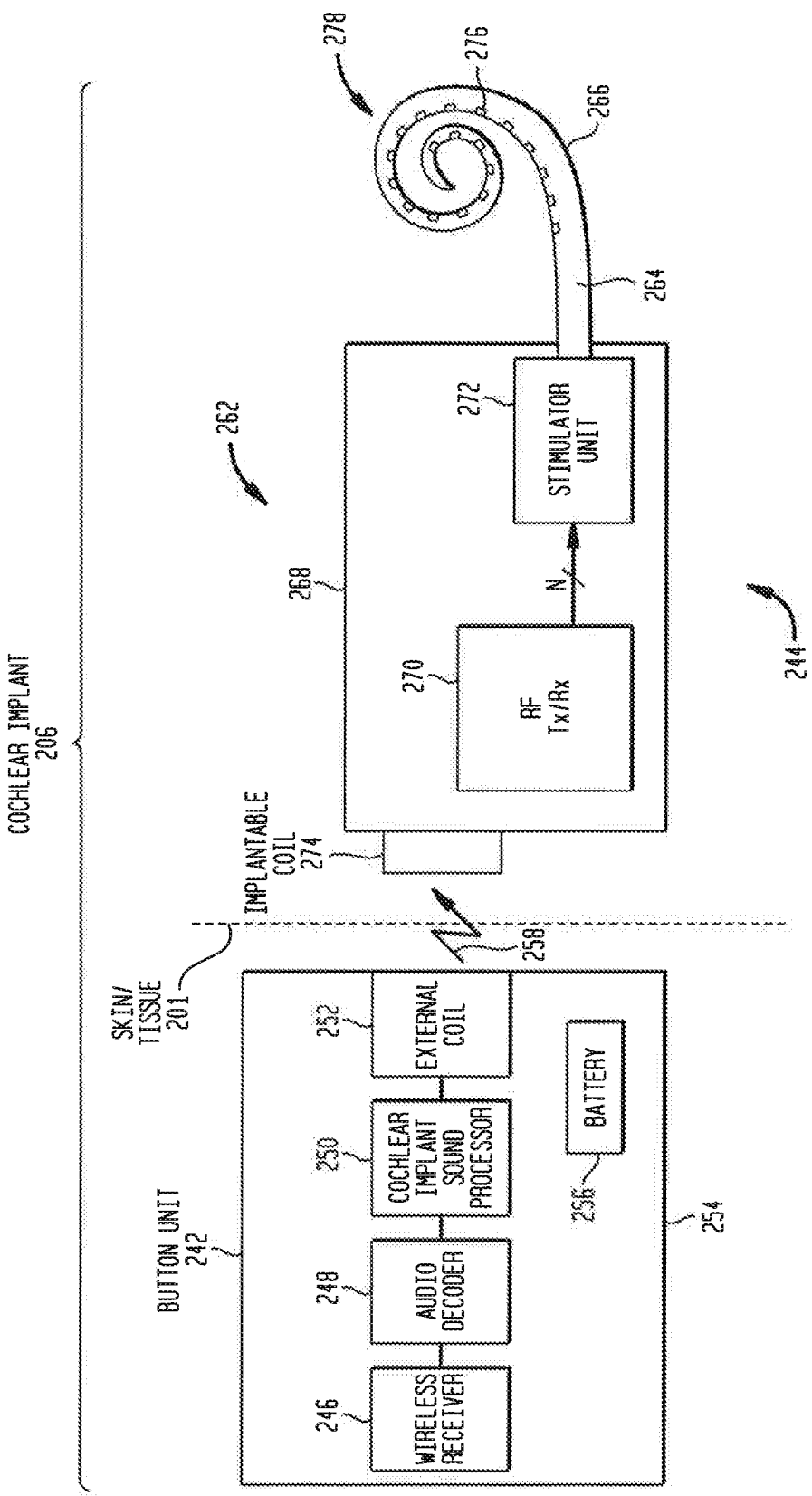
FIG. 2B is a block diagram of a cochlear implant configured to receive signals from a stand-alone hearing aid adapter in accordance with embodiments presented herein.

FIG. 2A is a block diagram illustrating one arrangement for a stand-alone hearing aid adapter in accordance with embodiments presented herein, which is shown in FIG. 2 as stand-alone hearing aid adapter 202. For completeness, FIG. 2A also illustrates an example arrangement for a conventional acoustic hearing aid 206. FIG. 2B illustrates an example arrangement for a cochlear implant 206 that may operate with the stand-alone hearing aid adapter 202 of FIG. 2A.

Referring first to the acoustic hearing aid 204, shown are two sound input elements in the form of microphones 214(A) and 214(B), an analog-to-digital (A/D) converter 216, a hearing aid sound processor 218, a digital-to-analog (D/A) converter 220, an amplifier 220, an acoustic receiver connector 224, and one or more batteries 223. The one or more batteries 223, which may be a disposable or rechargeable batteries, are configured to supply power to the other elements of the acoustic hearing aid 204.

The microphones 214(A) and 214(B) are configured to detect ambient sound signals 211 and to generate electrical signals therefrom. It is to be appreciated that, in addition to the two microphones 214(A) and 214(B), acoustic hearing aids may also include other sound input elements, such as telecoils, audio input ports, etc. However, merely for ease of illustration, these other types of sound input elements have been omitted from FIG. 2A.

Returning to the example arrangement of FIG. 2A, the electrical signals generated by the microphones 214(A) and 214(B) are provided to the A/D converter 216 which converts the electrical signals generated by the microphones 214(A) and 214(B) from the analog domain to the digital domain. The A/D converter 216 provides the resulting digital signals to a hearing aid sound processor 218.

The hearing aid sound processor 218 is, for example, a digital signal processor (DSP) that is generally configured to process and refine the digital signals before conversion back into an acoustic sound. For example, the hearing aid sound processor 218 may be configured to perform noise reduction/speech enhancement (e.g., execute adaptive algorithms, emphasize sounds of particular frequency, etc.), execute anti-feedback control mechanisms, perform automatic switching between different listening programs, among other operations. However, regardless of the specific operations performed, the hearing aid sound processor 218 outputs digital signals that are processed (e.g., enhanced) versions of the ambient sound signals detected by the microphones 214(A) and 214(B) (i.e., generates processed sound signals).

The processed sound signals generated by the hearing aid sound processor 218 are provided to a D/A converter 220 that converts the processed sound signals from the digital domain to the analog domain. An amplifier 222 amplifies the processed analog signals to generate amplified processed sound signals, which are then provided to an acoustic receiver connector (receiver connector) 224. The receiver connector 224 is an element that enables an acoustic receiver (e.g., speaker) to be detachably electrically connected thereto to the elements of the acoustic hearing aid 204. In certain examples, the receiver connector 224 is a single or multi-pin/wire port, receptacle, socket, or other female connector portion that is configured to mate with a corresponding male connector portion, such a single or multi-pin/wire plug, jack, pin, etc., of an acoustic receiver. In other examples, the receiver connector 224 is a male connector portion that is configured to mate with a corresponding female connector portion of an acoustic receiver.

In a number of conventional acoustic hearing aids, the receiver connector 224 represents the exit point for processed (and amplified) signals generated by the acoustic hearing aid 204 within the electric domain As such, the signals provided to the receiver connector 224 are sometimes referred to herein as hearing aid electric output signals.

However, as shown in FIG. 2A, no acoustic receiver is connected to the receiver connector 224. Instead, the stand-alone hearing aid adapter 202 is connected to the acoustic hearing aid 204 via the receiver connector 224. More specifically, the stand-alone hearing aid adapter 202 comprises an adapter connector 226 that has an arrangement so as to mechanically and electrically mate with the receiver connector 224. As such, the stand-alone hearing aid adapter 202 receives the hearing aid output signals (i.e., the processed analog signals generated by the acoustic hearing aid 204).

As noted above, the receiver connector 224 may have different arrangements (e.g., comprise a male or female connector portion). As such, an adapter connector 226 in accordance with embodiments presented herein may also have different arrangements so as to properly mate with the receiver connector 224.

The stand-alone hearing aid adapter 202 includes an adaption module 215 that is configured to convert the hearing aid electric output signals into input signals useable by the cochlear implant 206 (shown in FIG. 2A), sometimes referred to herein as implantable hearing prosthesis input signals. In the embodiment of FIG. 2A, the adaption module 215 comprises an A/D converter 228 and an audio encoder 230. The A/D converter 228 is configured to convert the hearing aid electric output signals from the analog domain to the digital domain. The audio encoder 230 is configured to compress the digital signals received from the A/D converter 228 (e.g., according to a given audio file format or streaming audio format). That is, in general, the audio encoder 230 executes an algorithm configured to represent the digital audio signal with a minimum number of bits while retaining the quality of the audio. In one form, the A/D converter 228 and the audio encoder 230 collectively form an audio codec.

The audio encoder 230 generates a compressed audio signal that is provided to a wireless transmitter or transceiver 232. The wireless transmitter 232 is configured to wirelessly transmit the compressed audio signals to the cochlear implant 206. In certain, embodiments the wireless transmitter 232 is a Bluetooth® or Bluetooth® Low Energy (BLE) transmitter that communicates using short-wavelength Ultra High Frequency (UHF) radio waves in the industrial, scientific and medical (ISM) band from 2.4 to 2.485 gigahertz (GHz). Bluetooth® is a registered trademark owned by the Bluetooth® SIG. However, it is to be appreciated that other types of wireless transmission may be used in alternative embodiments.

As noted above, the compressed audio signals represent a processed (enhanced) digital version of the sound signals received by the sound input elements (e.g., microphones 214(A) and 214(B)) of the acoustic hearing aid 204. In addition, as described further below, the compressed audio signals are useable by the cochlear implant 206 for generation and delivery of stimulation signals to a recipient. As such, the compressed audio signals are sometimes referred to herein as implantable hearing prosthesis input signals and are represented in FIGS. 2A and 2B by arrow 212.

As noted, FIG. 2B illustrates an example arrangement for a cochlear implant 206 that may operate with the stand-alone hearing aid adapter 202 of FIG. 2A. The cochlear implant 206 of FIG. 2B includes an external component 242 and an internal/implantable component 244, although other arrangements may have a totally-implantable configuration. The external component 242 is configured to be directly or indirectly attached to the body of a recipient, while the implantable component 244 is configured to be subcutaneously implanted within the recipient (i.e., under the skin/tissue 201 of the recipient).

Traditionally, external components of a cochlear implant have been formed by two elements, a behind-the-ear unit and a separate coil unit, which are connected by a cable. In these traditional arrangements, any sound input elements, sound processing elements, power sources, etc. are housed in a behind-the-ear component, while the separate coil unit includes a radio-frequency (RF) coil for use in transcutaneous communication with the implantable component. However, in the example of FIG. 2B, the external component 242 is a so-called "button" unit where the sound processing elements, power source, external coil, etc. are integrated into a single housing. As noted below, the button unit 242 also includes a magnet and is configured to be worn at a location where this magnet can be magnetically coupled to an implantable magnet. Although FIG. 2B illustrates the external component 242 as a button unit, it is to be appreciated that the external component 242 may have other arrangements.

The button unit 242 comprises a wireless receiver or transceiver 246, an audio decoder 248, a cochlear implant processor 250, an external coil 252, a battery 256, and a magnet (not shown in FIG. 2B) fixed relative to the external coil 252. The wireless receiver 246 is configured for communication with the wireless transmitter 232 (FIG. 2A) in the stand-alone hearing aid adapter 202 so as to wirelessly receive the implantable hearing prosthesis input signals 212. The audio decoder 248 is configured to decompress the implantable hearing prosthesis input signals 212 (e.g., according to a given audio file format or streaming audio format). That is, in general, the audio decoder 248 executes an algorithm to reverse the compression performed by the audio encoder 230 in the stand-alone hearing aid adapter 202. The decompressed signals are then provided to the cochlear implant processor 250. The encoded output signals representative of electrical stimulation, which are represented in FIG. 2B by arrow 258, are transmitted to the implantable component 244 via a closely coupled radio frequency (RF) link (e.g., a 5 megahertz (MHz) inductive RF link).

As described further below, the cochlear implant processor 250 executes one or more operations to convert the decompressed signals received from the audio decoder 248 into encoded output signals that represent electric (current) stimulation for delivery to the recipient. Also as described below, the number and types of operations performed by the cochlear implant processor 250 may vary in different embodiments, but generally include sound coding operations. In certain embodiments, the cochlear implant processor 250 may execute sound processing operations.

As shown in FIG. 2B, the implantable component 244 comprises an implant body (main module) 262, a lead region 264, and an elongate intra-cochlear stimulating assembly 266. The implant body 262 generally comprises a hermetically-sealed housing 268 in which an internal RF transceiver unit (transceiver) 270 and a stimulator unit 272 are disposed. The implant body 262 also includes an internal/implantable coil 274 that is generally external to the housing 268, but which is connected to the RF transceiver 270 via a hermetic feedthrough (not shown in FIG. 2B). Implantable coil 274 is typically a wire antenna coil comprised of multiple turns of electrically insulated single-strand or multi-strand platinum or gold wire. The electrical insulation of implantable coil 274 is provided by a flexible molding (e.g., silicone molding), which is not shown in FIG. 2B. Generally, a magnet is fixed relative to the implantable coil 274 for magnetic coupling with the magnet in the button sound processing unit 242.

Elongate stimulating assembly 266 is configured to be at least partially implanted in the recipient's cochlea (not shown) and includes a plurality of longitudinally spaced intra-cochlear electrical stimulating contacts (electrodes) 276 that collectively form a contact array 278 for delivery of electrical stimulation (current) to the recipient's cochlea. Stimulating assembly 266 extends through an opening in the cochlea (e.g., cochleostomy, the round window, etc.) and has a proximal end connected to stimulator unit 272 via lead region 264 and a hermetic feedthrough (not shown in FIG. 2B). Lead region 264 includes a plurality of conductors (wires) that electrically couple the electrodes 276 to the stimulator unit 272.

As noted, the output signals 258 are sent to the implantable component 244 via a closely-coupled RF link formed by the external coil 252 and the implantable coil 274. More specifically, the magnets fixed relative to the external coil 252 and the implantable coil 274 facilitate the operational alignment of the external coil 252 with the implantable coil 274. This operational alignment of the coils enables the external coil 252 to transmit the encoded data signals 258, as well as power signals received from battery 256, to the implantable coil 274.

In general, the encoded data signals 258 are received at the RF transceiver 270 where they are converted into output signals for the stimulator unit 272. The stimulator unit 272 is configured to utilize the output signals received from the RF transceiver 270 to generate electrical stimulation signals (e.g., current signals) for delivery to the recipient's cochlea via one or more stimulating contacts 276. In this way, cochlear implant 206 electrically stimulates the recipient's auditory nerve cells, bypassing absent or defective hair cells that normally transduce acoustic vibrations into neural activity, in a manner that causes the recipient to perceive one or more components of the received sound signals.

As noted, FIG. 2B illustrates a cochlear implant having both external and implantable components. However, it is to be appreciated that embodiments presented herein may include totally implantable cochlear implants where all components of the cochlear implant are configured to be implanted under the skin/tissue of a recipient. In these embodiments, the elements shown as part of the button unit in FIG. 2B, including the wireless receiver, audio decoder, cochlear implant processor, and battery would be included in the implantable component. Because all components of totally implant cochlear implant are implantable, such cochlear implants operate, for at least a finite period of time, without the need of an external device.

As detailed above, in the arrangements of FIGS. 2A and 2B, as well in arrangements that make use of a totally implantable cochlear implant, the sound signals that are used by the cochlear implant 206 to generate the electrical stimulation signals for delivery to the recipient are first detected by the acoustic hearing aid 204. The acoustic hearing aid 204 performs hearing aid processing operations on these received sound signals and the processed sound signals are then sent to the cochlear implant 206 via the stand-alone adapter 202. In other words, in accordance with the above embodiments, the stand-alone hearing aid adapter 202 converts the conventional acoustic hearing aid 204 into a streaming ambient sound/audio source for the cochlear implant 206. Stated differently, the stand-alone hearing aid adapter 202 wirelessly streams an enhanced version of ambient sounds from the hearing aid to the cochlear implant 206, thereby allowing the recipient to continue to use his/her acoustic hearing aid, including the controls, programs, etc. associated with the hearing aid, even after he/she receives the cochlear implant 206.

As noted above, hearing aid adapters in accordance with the embodiments presented herein are "stand-alone" adapters, meaning that the adapters operate independent from both the acoustic hearing aid and the cochlear implant that are linked by the adapter. For example, the stand-alone hearing aid adapter 202 includes one or more internal batteries (e.g., replaceable or rechargeable batteries) 234 so that it does not need to draw power from either the acoustic hearing aid or the cochlear implant. In addition, the hearing aid adapters in accordance with the embodiments presented herein are not required to be aware of the specific processing or other operations performed at either the acoustic hearing aid or the cochlear implant.

Similarly, the acoustic hearing aid and, in certain examples, the cochlear implant, need not be aware of the presence or use of the hearing aid adapter. In particular, the acoustic hearing aid merely performs its standard operations to output a signal to its receiver connector, and the acoustic hearing has no knowledge of subsequent operations. Moreover, from the perspective of the cochlear implant, the signal received from the stand-alone adapter can be interpreted as a streaming audio source.

Due to the stand-alone nature of the hearing aid adapters presented herein, the adapters can operate with hearing aids and cochlear implants of different makes (i.e., different manufacturers) and models, including enabling the interoperation of acoustic hearing aids and cochlear implants from different manufacturers. As a result of the ability to operate with, and enable interoperation by, different makes/models of hearing aids and cochlear implants, the stand-alone hearing aid adapters presented herein are sometimes referred to as "universal" hearing-aid adapters.

The stand-alone/universal nature of the hearing aid adapters presented herein may have several advantages. For example, not only do the stand-alone hearing aid adapters presented herein enable a recipient to continue using his/her acoustic hearing aid and accessories when upgrading to a cochlear implant, but the adapters presented herein may also enable implantable hearing prosthesis manufactures to rapidly leverage hearing aid technology when delivering new products as well as develop lower cost implantable solutions.

Figure 3:
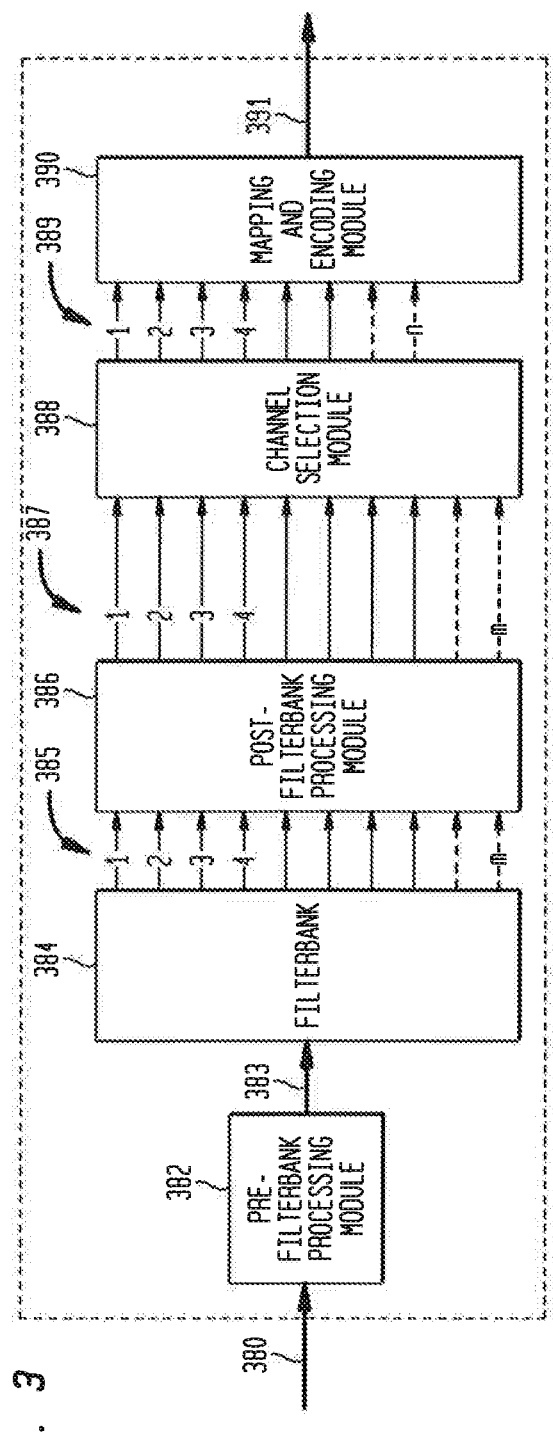
FIG. 3 is a block diagram of a cochlear implant sound processor configured to process signals received from a stand-alone hearing aid adapter in accordance with embodiments presented herein.

FIG. 3 is a block diagram illustrating details of a cochlear implant processor 350 that, in certain examples, can function as the cochlear implant processor 250 of FIG. 2B. More particularly, the cochlear implant processor 350 may utilize signals 380 received from a stand-alone hearing aid adapter in accordance with embodiments presented herein. As shown, the cochlear processor 350 comprises a pre-filterbank processing module 382, a filterbank 384, a post-filterbank processing module 386, a channel selection module 388, and a channel mapping module 390. The pre-filterbank processing module 382 receives the signals 380 sent from a stand-alone adapter via a wireless receiver and decoder (not shown in FIG. 3) and is configured to, as needed, prepare those signals for subsequent processing. The pre-filterbank processing module 382 generally includes broadband automatic gain control and frequency shaping and generates a pre-filtered input signal 383 that is provided to the filterbank 384.

The filterbank 384 uses the pre-filtered input signal 383 to generate a suitable set of bandwidth limited channels, or frequency bins, that each includes a spectral component of the received sound signals that are to be utilized for subsequent sound processing. That is, the filterbank 384 is a plurality of band-pass filters that separates the pre-filtered input signal 383 into multiple components, each one carrying a single frequency sub-band of the original signal (i.e., frequency components of the received sounds signal as included in pre-filtered input signal 383).

The channels created by the filterbank 384 are sometimes referred to herein as processing channels, and the sound signal components within each of the processing channels are sometimes referred to herein in as band-pass filtered signals or channelized signals. As described further below, the band-pass filtered or channelized signals created by the filterbank 384 may be adjusted/modified as they pass through the processing path. As such, the band-pass filtered or channelized signals are referred to differently at different stages of the processing path. However, it will be appreciated that reference herein to a band-pass filtered signal or a channelized signal may refer to the spectral component of the received sound signals at any point within the processing path (e.g., pre-processed, processed, selected, etc.).

At the output of the filterbank 384, the channelized signals are initially referred to herein as pre-processed signals 385. The number 'm' of channels and pre-processed signals 385 generated by the filterbank 384 may depend on a number of different factors including, but not limited to, implant design, number of active electrodes, coding strategy, and/or recipient preference(s). In certain arrangements, twenty-two (22) channelized signals are created and the cochlear implant processor 350 is said to include 22 channels.

In the example of FIG. 3, the cochlear implant processor 350 also includes a post-filterbank processing module 386. The post-filterbank processing module 386 is configured to perform a number of sound processing operations on the pre-processed signals 385. These sound processing operations may include, for example gain adjustments (e.g., multichannel gain control), noise reduction operations, signal enhancement operations (e.g., speech enhancement), etc., in one or more of the channels. As used herein, noise reduction is refers to processing operations that identify the "noise" (i.e., the "unwanted") components of a signal, and then subsequently reduce the presence of these noise components. Signal enhancement refers to processing operations that identify the "target" signals (e.g., speech, music, etc.) and then subsequently increase the presence of these target signal components. Speech enhancement is a particular type of signal enhancement. After performing the sound processing operations, the post-filterbank processing module 386 outputs a plurality of processed channelized signals 387.

In the embodiment of FIG. 3, the channel selection module 388 selects a subset 'n' of the 'm' processed channelized signals 387 for use in generation of stimulation for delivery to a recipient (i.e., the sound processing channels are reduced from 'm' channels to 'n' channels). In one specific example, the 'n' largest amplitude channels (maxima) from the 'm' available combined channel signals/masker signals is made, with 'm' and 'n' being programmable during cochlear implant fitting, and/or operation of the cochlear implant. It is to be appreciated that different channel selection methods could be used, and are not limited to maxima selection. The signals selected at channel selection module 388 are represented in FIG. 3 by arrows 389 and are referred to as selected channelized signals or, more simply, selected signals.

The cochlear implant processor 350 also comprises the channel mapping module 390. The channel mapping module 390 is configured to map the amplitudes of the selected signals 389 into a set of stimulation commands that represent the attributes of stimulation signals (current signals) that are to be delivered to the recipient so as to evoke perception of the received sound signals. This channel mapping may include, for example, threshold and comfort level mapping, dynamic range adjustments (e.g., compression), volume adjustments, etc., and may encompass sequential and/or simultaneous stimulation paradigms.

In the embodiment of FIG. 3, the set of stimulation commands that represent the stimulation signals are encoded for transcutaneous transmission (e.g., via an RF link) to an implantable component (not shown). This encoding is performed, in the specific example of FIG. 3, at channel mapping module 390. As such, channel mapping module 390 is sometimes referred to herein as a channel mapping and encoding module and operates as an output block configured to convert the plurality of channelized signals into a plurality of output signals 391. The output signals 391 comprise a plurality of encoded signals for delivery to the implantable component via an RF coil.

Figure 4:
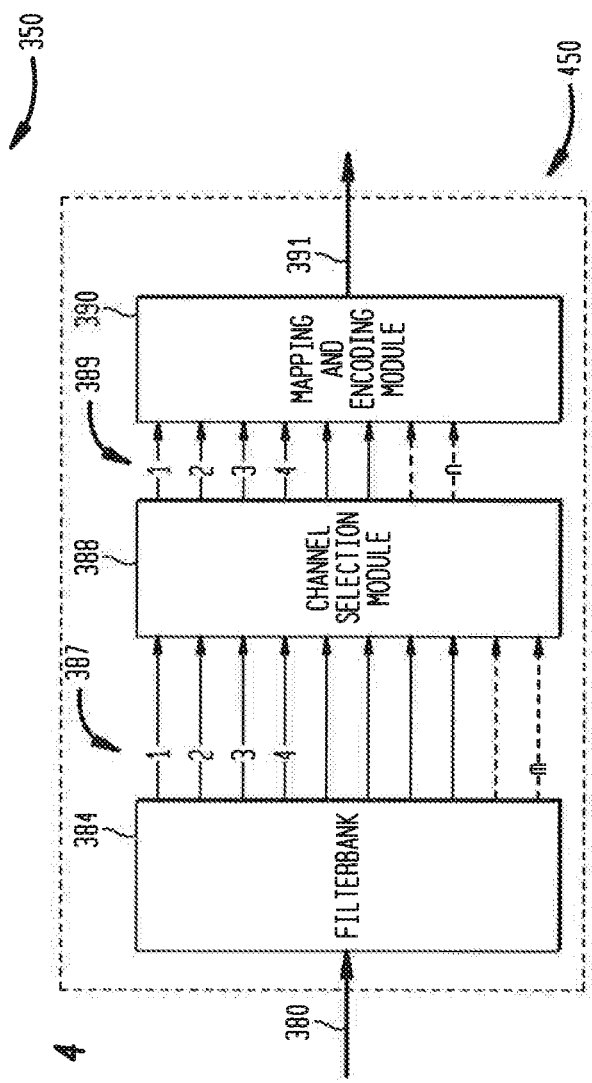
FIG. 4 is a block diagram of another cochlear implant sound processor configured to process signals received from a stand-alone hearing aid adapter in accordance with embodiments presented herein.

FIG. 3 illustrates a cochlear implant processor that implements a complete or full sound processing path that is operable to convert sound signals received from a stand-alone adapter, as well as signals from other sound sources (e.g., microphones), into encoded output signals. That is, cochlear implant processor 350 of FIG. 3 may be referred to as a "sound processor" because it performs sound processing operations (i.e., the operations of the post-filterbank processing module 386). In contrast, FIG. 4 is a block diagram illustrating details of a simplified cochlear implant processor 450 that, in certain examples, can function as the cochlear implant processor 250 of FIG. 2B. In the example of FIG. 4, the cochlear implant processor 450 does not perform sound processing operations and represents a processor that is specifically designed to process signals 380 received from a stand-alone hearing aid adapter in accordance with embodiments presented herein.

More specifically as shown, the cochlear implant processor 450 comprises a filterbank 384, a channel selection module 388, and a channel mapping module 390, that each operate similar to the filterbank, channel selection module, and mapping and encoding module, respectively, described above with reference to FIG. 3. However, as shown, the pre-filterbank processing module 382 and the post-filterbank processing module 386 present in the cochlear implant processor 350 (FIG. 3) are not present in cochlear implant processor 450. The cochlear implant processor 450 does not include a pre-filterbank processing module or a post-filterbank processing module because these operations are performed by the acoustic hearing aid processor. In other words, since the sound processor 450 operates only on signals received from a stand-alone hearing aid adapter, the pre-filterbank processing and post-filterbank processing operations are redundant to the operations performed by the acoustic hearing aid and, as such, are not needed.

In certain embodiments, the arrangement of FIG. 4 may be implemented as a static configuration within a cochlear implant. That is, the cochlear implant is specifically configured to operate exclusively with (on) signals received from a stand-alone hearing aid adapter (i.e., signals streamed from an acoustic hearing aid).

In other embodiments, the arrangement of FIG. 4 may be implemented as a specific operational mode (i.e., a "simplified mode") of a full-featured cochlear implant processor (e.g., as a specialized mode of a cochlear implant processor that has all of the functionality shown in FIG. 3). In other words, the arrangement of FIG. 4 could be implemented by the cochlear implant processor 350 of FIG. 3 by configuring the cochlear implant processor 350 to skip, eliminate, or otherwise bypass the pre-filterbank processing and post-filterbank processing operations. In these embodiments, the cochlear implant processor 350 could be locked to operate in the simplified mode (e.g., by a user) and then switched to a full-featured mode the acoustic hearing aid (and adapter) are no longer used. Alternatively, the cochlear implant processor 350 could be configured to dynamically switch between the simplified mode when the cochlear implant processor 350 detects signals received from a hearing aid adapter (i.e., signals received at a wireless receiver) and a full-featured mode when signals are received from other sound sources.

Figure 5:
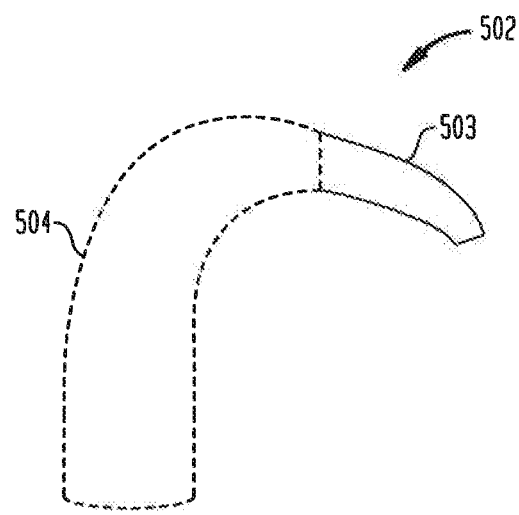
FIG. 5 is a schematic diagram illustrating an arrangement for a stand-alone hearing aid adapter in accordance with embodiments presented herein.

Stand-alone hearing aid adapters in accordance with embodiments of the present invention may have a number of different physical arrangements for use with an acoustic hearing aid. For example, FIG. 5 illustrates a stand-alone hearing aid adapter 502 having a housing 503 formed as an earhook attachment for a behind-the-ear (BTE) acoustic hearing aid 504. Located within the housing 503 are the functional components of the stand-alone hearing aid adapter 502 (e.g., A/D converter, audio encoder, wireless transmitter, battery, etc.).

In this arrangement of FIG. 5, the stand-alone hearing aid adapter 502 is configured to both electrically and physically mate with the BTE acoustic hearing aid 504 via the receiver connector of the hearing aid (not shown in FIG. 5). The physical connection/mating between the stand-alone hearing aid adapter 502 and the BTE acoustic hearing aid 504 is substantially rigid such that the-alone hearing aid adapter assists in retaining the hearing aid on the recipient's ear (i.e., rests on the recipient's outer ear).

Figure 6:
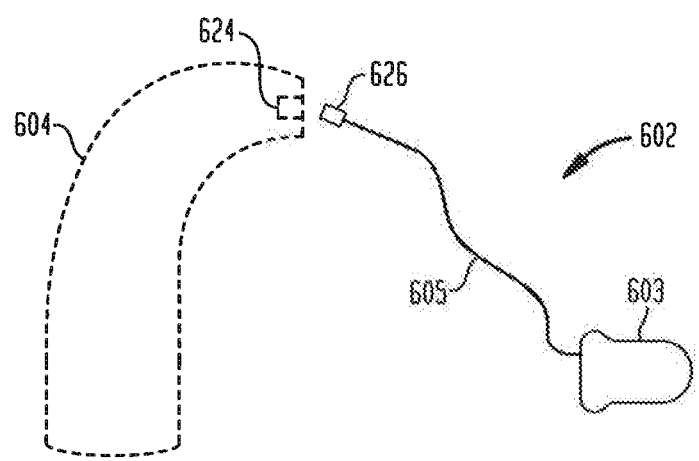
FIG. 6 is a schematic diagram illustrating another arrangement for a stand-alone hearing aid adapter in accordance with embodiments presented herein.

FIG. 6 illustrates a stand-alone hearing aid adapter 602 that is configured as an in-the-ear (ITE) component. In this arrangement of FIG. 6, the stand-alone hearing aid adapter 602 comprises a housing 603 that has a shape so as to be inserted and retained into the recipient's outer ear. Located within the housing 603 are the functional components of the stand-alone hearing aid adapter 602 (e.g., A/D converter, audio encoder, wireless transmitter, battery, etc.). The stand-alone hearing aid adapter 602 also includes a wire 605 that extends from the housing 603 to an adapter connector 626 that is configured to mechanically and electrically interface with a receiver connector 624 in an acoustic hearing aid 604. In other words, in the arrangement of FIG. 6, the functional components of the stand-alone hearing aid adapter 602 are located within the recipient's outer ear and are electrically connected to the acoustic hearing aid 604 that is, for example, a BTE hearing aid worn on the recipient's outer ear.

As noted above, stand-alone hearing aid adapters in accordance with embodiments presented herein may have a number of different physical arrangements that are useable to enable interoperation of an acoustic hearing aid with a cochlear implant or other implantable hearing prosthesis. As such, it is to be appreciated that the arrangements shown in FIGS. 5 and 6 are illustrative.

Figure 7:
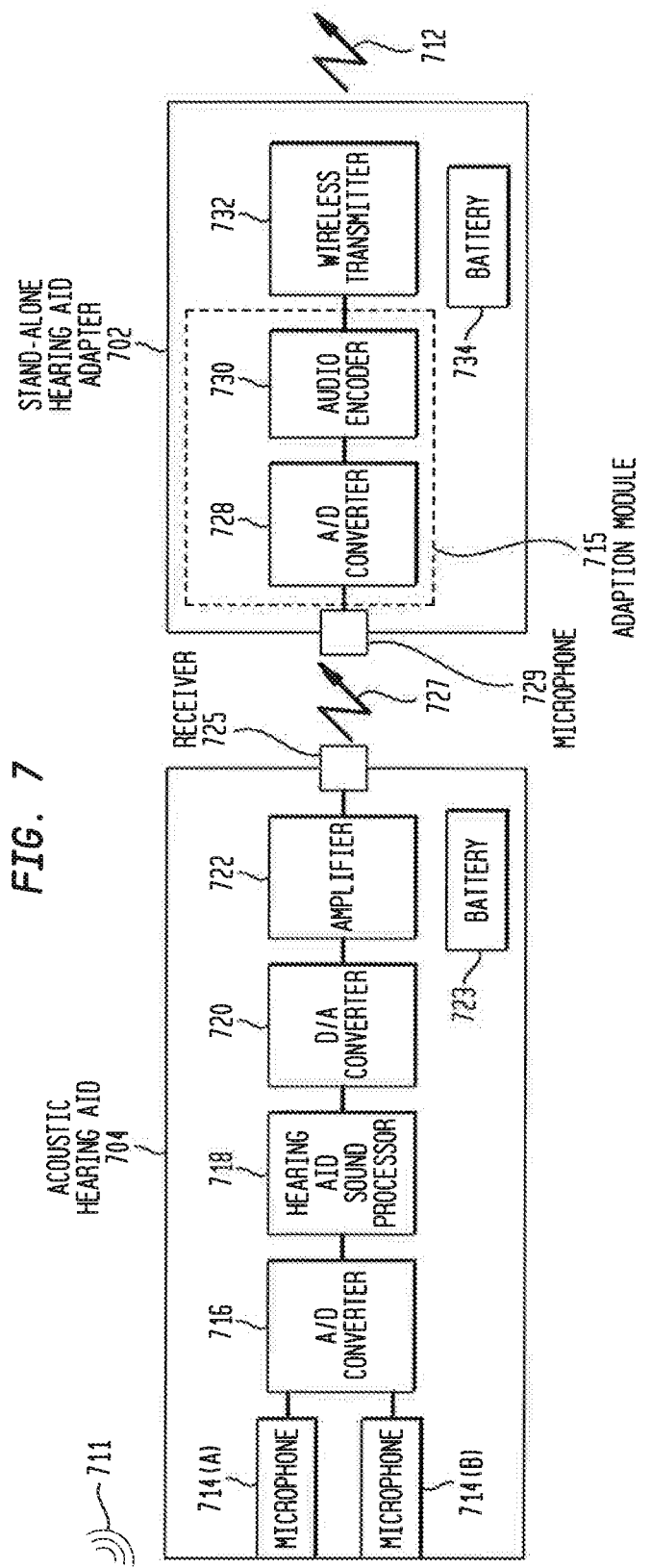
FIG. 7 is a block diagram of a stand-alone hearing aid adapter in accordance with embodiments presented herein.

The stand-alone hearing adapters in accordance with embodiments presented herein have primarily described above with reference to a physical electrical connection between the hearing aid and the adapter, where the adapter connects at the location of a detachable acoustic receiver (i.e., the adapter replaces the acoustic receiver). In certain embodiments presented herein, stand-alone hearing aid adapters may be configured to use an acoustic coupling, rather than an electric coupling, with a hearing aid. One such example arrangement is shown in FIG. 7 as stand-alone hearing aid adapter 702. For completeness, FIG. 7 also illustrates an example arrangement for a conventional acoustic hearing aid 704 that may operate with the stand-alone hearing aid adapter 702.

Referring first to the acoustic hearing aid 704, shown are two sound input elements in the form microphones 714(A) and 714(B), an A/D converter 716, a hearing aid sound processor 718, a D/A converter 720, an amplifier 722, a battery 723, and an acoustic receiver 725. As noted, the acoustic hearing aids may also include other sound input elements, such as telecoils, audio input ports, etc. which, for ease of illustration, have been omitted from FIG. 7.

The microphones 714(A) and 714(B) are configured to detect ambient sound signals 711 and to generate electrical signals therefrom. The electrical signals generated by the microphones 714(A) and 714(B) are provided to the A/D converter 716 for conversion from the analog domain to the digital domain. The resulting digital signals are then provided to the hearing aid sound processor 718. The hearing aid sound processor 718 is, for example, a digital signal processor (DSP) that is generally configured to process and refine the digital signals before conversion back into an acoustic sound. The hearing aid sound processor 718 outputs digital signals that are processed (e.g., enhanced) versions of the sound signals received by the microphones 714(A) and 714(B) (i.e., processed sound signals).

The processed sound signals generated by the hearing aid sound processor 718 are provided to the D/A converter 720 for conversion from the digital domain to the analog domain. The amplifier 722 amplifies the processed analog signals to generate amplified signals, which are then provided to the acoustic receiver (e.g., speaker) 725. The acoustic receiver 725 uses the amplified signals to generate acoustic sound signals 727 that represent a processed/enhanced and amplified version of the sound signals 711 originally received by the microphones 714(A) and 714(B). The acoustic sound signals 727 are sometimes referred to herein as hearing aid acoustic output signals.

As shown in FIG. 7, the stand-alone hearing aid adapter 702 includes one or more microphones 729 that are configured to resample the hearing aid acoustic output signals 727 generated by the acoustic receiver 725. That is, the one or more microphones 729 receive the hearing aid acoustic output signals 727 via an acoustic coupling with the hearing aid 704. The one or more microphones 729 are configured to generate electrical signals based on the hearing aid acoustic output signals 727.

The stand-alone hearing aid adapter 702 includes an adaption module 715 that is configured to convert the hearing aid acoustic output signals 727 into input signals useable by a cochlear implant (not shown in FIG. 7). In the embodiment of FIG. 7, the adaption module 715 comprises an A/D converter 728 that is configured to convert the electrical signals generated by the one or more microphones 729 from the analog domain to the digital domain. The adaption module 715 also comprises an audio encoder 730 that is configured to compress the digital signals received from the A/D converter 728. That is, in general, the audio encoder 730 executes an algorithm configured to represent digital audio signal with a minimum number of bits while retaining the quality of the audio. In one form, the A/D converter 728 and the audio encoder 730 collectively form an audio codec.

The audio encoder 730 generates a compressed audio signal that is provided to a wireless transmitter 732. The wireless transmitter 732 is configured to wirelessly transmit the compressed audio signals to the cochlear implant 706. In certain, embodiments the wireless transmitter 732 is a Bluetooth® or BLE transmitter that communicates using short-wavelength UHF radio waves in the ISM band from 2.4 to 2.485 GHz. Bluetooth® is a registered trademark owned by the Bluetooth® SIG. However, it is to be appreciated that other types of wireless transmission may be used in alternative embodiments.

As noted above, the compressed audio signals represent a processed (enhanced) version of the sound signals received by the sound input elements (e.g., microphones 714(A) and 714(B)) of the acoustic hearing aid 704. In addition, the compressed audio signals are useable by the cochlear implant for generation and delivery of stimulation signals to a recipient. As such, the compressed audio signals are sometimes referred to herein as cochlear implant input signals, and are represented in FIG. 7 by arrow 712.

The use of a stand-alone hearing aid adapter in accordance with embodiments present herein may also enable a simplified cochlear implant fitting procedure where a maximum comfort level (C level) could set, for example, with a single Master Volume type control, and the fine tuning could then be handled by the hearing fitting software, including measuring hearing thresholds (T levels), etc. More specifically, in accordance with embodiments presented herein, once a C-Level is set for the cochlear implant sound processor, further audiological programming could exclusively focus on the hearing aid, and be performed by an audiologist only familiar with hearing aid technology. For example, if the recipient is having difficulty hearing soft-sounds, then the gain at low sound-pressure levels could be increased in the hearing aid programming software by the audiologist and applied to the hearing aid. This would flow through to the cochlear implant without creating any discomfort since the C-Levels are untouched, resolving the problem. This sort of approach is only relevant when the cochlear implant is used with the hearing aid as the front-end system, which is enabled by the stand-alone adapter.

This approach can be extended to follow a complete hearing aid programming methodology whereby the hearing thresholds are first measured at a set of frequencies, resulting in the recipient's audiogram. This audiogram is then used to prescribe hearing aid gains which can be further adjusted by the audiologist based on their clinical practice and are ultimately programmed into the device. In this mode, the cochlear implant sound processor is initially set up with the recipient's C-levels which is just setting the upper bound of comfortable stimulation. In one example, the recipient can complete this step themselves using a Master Volume control on a remote control, mobile phone, etc. In these examples, the device also be 'by default' configured with very low T-levels which would typically be below the true threshold of hearing perceived by the recipient. The hearing thresholds are instead measured within the hearing-aid software suite and methodology.

Figure 8:
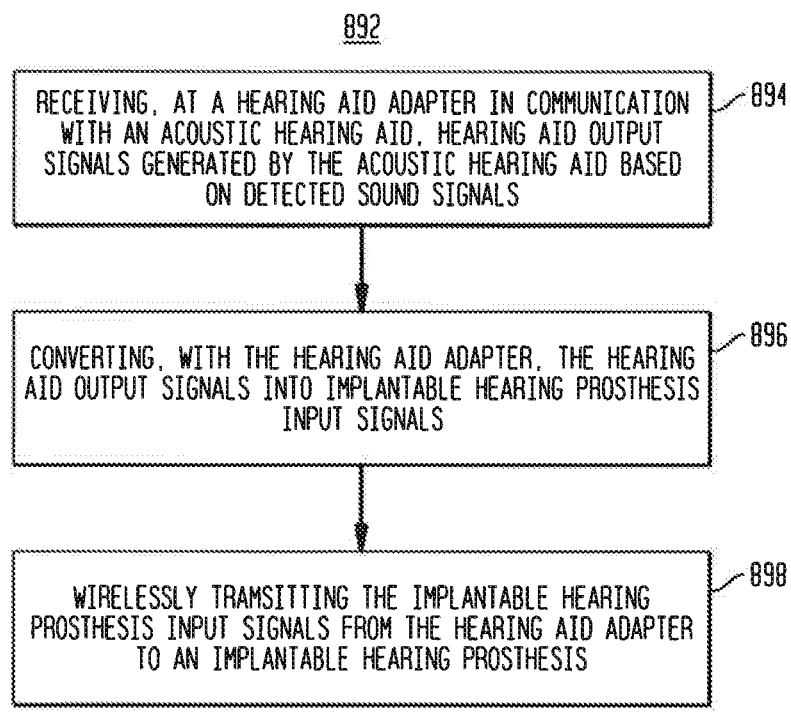
FIG. 8 is a flowchart of a method in accordance with embodiments presented herein.

FIG. 8 is a flowchart of a method 892 in accordance with embodiments presented herein. Method 892 begins at 894 where a hearing aid adapter in communication with an acoustic hearing aid receives hearing aid output signals generated by the acoustic hearing aid based on detected sound signals. At 896, the hearing aid adapter converts the hearing aid output signals into implantable hearing prosthesis input signals. At 898, the implantable hearing prosthesis input signals are wirelessly transmitted from the hearing aid adapter to an implantable hearing prosthesis.

In certain arrangements, a stand-alone hearing aid adapter enables a recipient to continue use of a hearing aid when transitioning to an implantable hearing prosthesis, such as a cochlear implant. The ability to continue use of the hearing aid has several advantages, including reduction in financial burden, elimination of the need to learn new controls or purchase new accessories, simplified fitting, etc. One additional benefit of a stand-alone hearing aid adapter in accordance with embodiments presented herein is the ability to enable bilateral communications with a contra-lateral prosthesis. Continued bilateral communications is difficult without the stand-alone hearing aid adapter as it is unlikely that a standard acoustic hearing aid would be able to wirelessly communicate with a standard cochlear implant processor.

It is to be appreciated that the embodiments presented herein are not mutually exclusive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A stand-alone hearing aid adapter, comprising:
   at least one input element configured to receive hearing aid output signals from an acoustic hearing aid;
   an adaption module configured to convert the hearing aid output signals into implantable hearing prosthesis input signal, wherein the adaption module comprises an analog-to-digital converter and an audio encoder; and
   a wireless transmitter configured to transmit the implantable hearing prosthesis input signals to an implantable hearing prosthesis.

2. The stand-alone hearing aid adapter of claim 1, wherein the hearing aid output signals are electrical signals, and wherein the at least one input element is an electrical connector configured to mate with an acoustic receiver connector of the acoustic hearing aid.

3. The stand-alone hearing aid adapter of claim 1, wherein the hearing aid output signals are acoustic signals transmitted by an acoustic receiver, and wherein the at least one input element is a microphone configured to sample the acoustic signals.

4. The stand-alone hearing aid adapter of claim 1, further comprising a housing forming an earhook that is configured for attachment to an outer ear of a recipient, wherein the adaption module and the wireless transmitter are located in the housing.

5. The stand-alone hearing aid adapter of claim 1, further comprising an in-the-ear housing configured to be inserted into an outer ear of a recipient, wherein the adaption module and the wireless transmitter are located in the in-the-ear housing.

6. The stand-alone hearing aid adapter of claim 1, further comprising a battery.

7. A method, comprising:
   receiving, at a hearing aid adapter in communication with an acoustic hearing aid, analog hearing aid output signals generated by the acoustic hearing aid based on detected sound signals;
   converting, with an analog-to-digital converter in the hearing aid adapter, the analog hearing aid output signals into digital signals;
   encoding, with an audio encoder in the hearing aid adapter, the digital signals into implantable hearing prosthesis input signals; and
   wirelessly transmitting the implantable hearing prosthesis input signals from the hearing aid adapter to an implantable hearing prosthesis.

8. The method of claim 7, further comprising:
   wirelessly receiving the implantable hearing prosthesis input signals at the implantable hearing prosthesis; and
   converting the implantable hearing prosthesis input signals into stimulation signals to evoke perception of the detected sound signals when delivered to a recipient of the implantable hearing prosthesis.

9. The method of claim 8, wherein the converting the implantable hearing prosthesis input signals into stimulation signals is performed without sound processing operations.

10. The method of claim 7, further comprising:
   detecting the sound signals at an acoustic hearing aid; and
   performing sound processing at the acoustic hearing aid to convert the detected sound signals into the hearing aid output signals.

11. The method of claim 7, wherein receiving the hearing aid output signals comprises:
   receiving electrical signals via an electrical connector configured to mate with an acoustic receiver connector of the acoustic hearing aid.

12. The method of claim 7, wherein receiving the hearing aid output signals at the hearing aid adapter comprises:
   receiving, via at least one input element, acoustic signals transmitted by an acoustic receiver, and wherein the at least one input element is a microphone configured to sample the acoustic signals.

13. An implantable hearing prosthesis system, comprising:
   an implantable hearing prosthesis configured to be at least partially implanted in a recipient; and
   a stand-alone hearing aid adapter configured to be coupled with an acoustic hearing aid and to wirelessly stream processed sound signals from the acoustic hearing aid to the implantable hearing prosthesis, wherein the stand-alone hearing aid adapter comprises an analog-to-digital converter and an audio encoder.

14. The implantable hearing prosthesis system of claim 13, wherein the stand-alone hearing aid adapter is electrically coupled to the acoustic hearing aid, and wherein the processed sound signals are received by the stand-alone hearing aid adapter as electrical signals.

15. The implantable hearing prosthesis system of claim 13, wherein the stand-alone hearing aid adapter is acoustically coupled to the acoustic hearing aid, and wherein the processed sound signals are received by the stand-alone hearing aid adapter as acoustic signals.

16. The implantable hearing prosthesis system of claim 13, wherein the stand-alone hearing aid adapter comprises:
   a housing forming an earhook that is configured for attachment to an outer ear of a recipient of the implantable hearing prosthesis, wherein a wireless transmitter is located in the housing for communication with a wireless receiver in the implantable hearing prosthesis.

17. The implantable hearing prosthesis system of claim 13, wherein the stand-alone hearing aid adapter comprises:
   an in-the-ear housing configured to be positioned in an outer ear of a recipient of the implantable hearing prosthesis, wherein a wireless transmitter is located in the in-the-ear housing for communication with a wireless receiver in the implantable hearing prosthesis, and wherein the analog-to-digital converter, audio encoder, and the wireless transmitter are located in the in-the-ear housing.

18. The implantable hearing prosthesis system of claim 13, wherein the implantable hearing prosthesis is configured to:
   wirelessly receive the processed sound signals from the stand-alone hearing aid adapter; and
   convert the processed sound signals into stimulation signals for delivery to a recipient of the implantable hearing prosthesis.

19. The implantable hearing prosthesis system of claim 13, wherein the implantable hearing prosthesis is a cochlear implant.

20. The implantable hearing prosthesis system of claim 19, wherein the implantable hearing prosthesis is a totally implantable cochlear implant having an implantable wireless receiver.

* * * * *